United States Patent [19]
Hosokawa et al.

[11] Patent Number: 5,972,905
[45] Date of Patent: Oct. 26, 1999

[54] USE OF OLIGOSACCHARIDES FOR THE TREATMENT OF PRURITUS CUTANEUS ASSOCIATED WITH RENAL FAILURE

[75] Inventors: Tomoyoshi Hosokawa; Kunio Ando, both of Kanagawa-ken; Tatsuro Shimaoka, Tochigi-ken; Tetsuo Nakamura, Tokyo, all of Japan

[73] Assignee: Institute of Immunology Co., Ltd., Tokyo, Japan

[21] Appl. No.: 08/973,969

[22] PCT Filed: Jun. 11, 1996

[86] PCT No.: PCT/JP96/01576

§ 371 Date: Feb. 20, 1998

§ 102(e) Date: Feb. 20, 1998

[87] PCT Pub. No.: WO97/00075

PCT Pub. Date: Jan. 3, 1997

[30] Foreign Application Priority Data

Jun. 14, 1995 [JP] Japan .................................. 7-180501

[51] Int. Cl.$^6$ .............................. A61K 31/70; C07H 3/04; C07H 3/06
[52] U.S. Cl. ................................ 514/53; 514/25; 514/54; 536/4.1; 536/123.1; 536/123.13
[58] Field of Search ................................ 536/123.13, 4.1, 536/123.1; 514/53, 25, 54

[56] References Cited

U.S. PATENT DOCUMENTS

3,793,461 2/1974 Yuen et al. ................................ 514/53

FOREIGN PATENT DOCUMENTS

4190764 7/1992 Japan .

OTHER PUBLICATIONS

Y. Matsuda et al., "Effect of Lactulose on Acute Renal Failure in Rabbits", Igaku to Yakugaku (Medicine and Pharmacy), vol. 27, No. 1, p. 49–54, 1992.

The Merck Index, Twelfth Edition, Merck & Co., Inc., 1996, p. 913.

*Primary Examiner*—Gary L. Kunz
*Attorney, Agent, or Firm*—Browdy and Neimark

[57] ABSTRACT

A pharmaceutical agent for improvement in pruritus cutaneus associated with renal failure and/or for the treatment of renal failure and/or its complications containing as an effective ingredient oligosaccharide or oligosaccharides such as, but not limited to fructo-oligosaccharide, galacto-oligosaccharide, isomalto-oligosaccharide, malto-oligosaccharide, lacto-sucrose and/or xylo-oligosaccharide, in particular, lactulose, rhamnose and lactitol.

7 Claims, No Drawings

USE OF OLIGOSACCHARIDES FOR THE TREATMENT OF PRURITUS CUTANEUS ASSOCIATED WITH RENAL FAILURE

TECHNICAL FIELD

This invention relates to a new pharmaceutical composition for alleviation of various syndromes, in particular pruritus cutaneus, characteristic to renal failure and hemodialysis patients.

BACKGROUND ART

Among the countries all over the world, the hemodialysis therapy is most widely practiced in Japan. This therapy over an extended time, however, induces various serious problems. The hemodialysis therapy for a long time, for example, causes the onset of complications such as cardiovascular disorder, anemia, abnormal bone metabolism, dysbolism, and/or immunodeficiency. In addition, it is said that 60–80% of the hemodialysis patients suffer from pruritus cutaneus. Although pruritus cutaneus itself does not impose direct threatening on the life of the patients, its persistent and chronic torment, night and day, is unbearable to the patients, both physically and mentally. From the view point of the maintenance and improvement in the quality of life, pruritus cutaneus is now a big problem in the treatment of the patients.

As a possible cause of pruritus cutaneus, 1. stimulation of the nerve ending by a certain substance accumulated in the blood by renal failure, 2. a decline in the pruritus threshold value due to change in the pH value, etc., or 3. abnormal secretion by the skin glands such as sebaceous glands and sweat glands, is suspected but it Is not yet clear what is responsible for it. For its treatment, antihistaminic agent is generally administered but it has limitation in its efficacy. Besides, due to its side effects like drowsiness, vertigo or generalized malaise, its administration must be discontinued in many cases. In addition, anti-allergic agent, adrenocortical agent or tranquilizer is administered but no agent alone can relieve the patients from the torment and establishment of an effective therapy has been expected.

DISCLOSURE OF INVENTION

The applicants of this invention have been conducting their research focusing on alleviation of pruritus cutaneus, among other complications, developed in renal failure patients treated with the hemodialysis therapy for a long time.

As the most potential substances that induce pruritus, recent studies suggest accumulation of uremic toxins and active oxygen. Since the removal rate of those substances by hemodialysis is very low, the applicants of this invention conducted clinical trials on the assumption that suppression of production of uremic toxins would prompt improvement in pruritus cutaneus.

As a result, administration of lactulose for one or two months decreased significantly toxic amino acid metabolites responsible for aggravation of uremia such as guanidino compounds like methylguanidine and guanidinosuccinic acid, indolacetic acid, p-cresol and declined methylguadinine/creatinine that is considered to be a physical active oxygen marker of the renal hemodialysis patients. The applicants of this invention found the correlation between the decrease in those uremic toxins and decline in the active oxygen marker and improvement in pruritus cutaneus, thus, completed this invention. This invention provides a pharmaceutical agent containing one, two or more kind or kinds of oligosaccharide or oligosaccharides as an effective ingredient for improvement in pruritus cutaneus associated with renal failure.

BEST MODE FOR CARRYING OUT THE INVENTION

Details of the invention are described below.

In addition to lactulose which has long been known as a growth factor of bifidobacteria, there have been found various kinds oligosaccharide that show the same effect. It is known that oligosaccharide such as, but not limited to, fructo-oligosaccharide, galactooligosaccharide, lactosucrose, maltooligosaccharide and xylooligosaccharide grow remarkably bifidobacteria in stool and reduce significantly toxic substances like ammonia, amine phenol and cresol in it. There has, however, been no report made so far on the effect of such oligosaccharide on the treatment of renal failure, in particular, on alleviation of pruritus. It is well known that ammonia is produced by deamination of part of protein or amino acids in the intestine by the intestinal bacteria and decomposition of lactulose by bifidobacteria or other intestinal bacteria in the large intestine help promote the production of organic acids like lactic acid, acetic acid, etc. which in turn decrease the pH value and inhibit absorption of ammonia. On account of this effect, lactulose has been used for the treatment of hyperammonemia. It is also known that administration of lactulose suppresses production of amines like phenol, skatole and indole in the intestine and promotes absorption of calcium in the small intestine. Nonetheless, the effect of lactulose on renal failure or its complications, especially pruritus cutaneus, has not been recognized. Renal hypofunction elicits uremic syndrome like insomnia, cephalea, vomiturition, renal anemia, hypertension and edema and they are treated with hemodialysis when they are not improved by the conservative treatment. As substances called uremic toxins that accumulate in the uremic patients and exacerbate the disease such as $\beta 2$-microglobulin, guanidine compounds, glycated proteins, indole compounds and phenol compounds have been reported. Removal of those toxins by hemodialysis, however, is not sufficient and can not necessarily mitigate pruritus cutaneus.

As the frequency of complications that develop in the patients treated with the hemodialysis treatment over a long period of time, cardiovascular complications are 50–60% and highest and cardiac failure is the highest cause of death. As complications that seriously affect the daily life of the renal failure patients, there are renal osteodystrophia, dialysis amyloidosis, anemia and pruritus cutaneus. A pharmaceutical agent under this invention is, among other complications associated with renal failure, most effective on alleviation of pruritus cutaneus. The patients treated with the hemodialysis therapy are held under various diet restrictions and are restricted to ingest salt, water, protein and potassium. Due to restriction of diet, many of the hemodialysis patients suffer from constipation or have difficulty in excretion.

The oligosaccharides in this invention activate intestinal peristalsis by promoting production of organic acids and improve excretion by softening stool. Furthermore, the oligosaccharides under this invention increase intestinal hydration by enhancing the intestinal osmotic pressure, thus enable smooth excretion. The oligosaccharide or oligosaccharides for a pharmaceutical agent under this invention for the treatment of pruritus cutaneus associated with renal failure and/or renal failure and its complications are a general term of oligosaccharide or oligosaccharides having 2 to about 10 monosaccharides glycosidically bonded and, according to the number of monosaccharides bonded, are classified as disaccharide, trisaccharide, tetrasaccharide, etc. In this invention, one, two or more kinds of oligosaccharides such as, but not limited to, fructooligosaccharide, galactooligosaccharide, isomaltooligosaccharide, maltooligosaccharide, lactosucrose and/or xylooligosaccharide used to achieve the purpose of this invention. Desirable oligosaccharides are disaccharides like, but not limited to, lactulose, trehalose, rhamnose and lactitol. Among those oligosaccharides, lactulose, in particular, is desirable.

Specifically, there is no limitation in the method of administration of the pharmaceutical agent under this invention for the treatment of renal failure, mitigation of pruritus cutaneus and/or improvement in laxation, but oral administration is desirable. Those saccharide or saccharides are supplied in crystal, amorphous powder, or syrup and can be administered to the patients in any form of pharmaceutical preparation like, but not limited to, granule, tablet, powder and syrup In such a pharmaceutical preparation, filler, extender, disintegrator, hemuctant, bonding agent and/or lubricant normally used can be added as required.

A daily dose of the pharmaceutical agent in this invention is, as an anhydride, in the range of 1 gram to 60 grams depending upon age, sex, body weight and symptom of the patients and normally 1 gram to 30 grams are preferred.

Example of Pharmaceutical Preparation

| | |
|---|---|
| Lactulose | 50 mg |
| Starch | 116 mg |
| Glyceric fatty acid ester | 30 mg |
| Cellulose | 2 mg |
| Silicon oxide | 2 mg |
| Total | 200 mg |

Detailed examples of this invention are described hereunder but they in no way limit the scope of this invention.

Example 1

A daily dose of 3 mg was administered orally to the healthy subjects aged 18 to 23 (male 5 and female 3) for 2 weeks and their stool was chronologically collected for the determination of ammonia, phenol, cresol, indole and skatole. Table 1 shows the results.

TABLE 1

Effect of lactulose on concentration of toxic substances in stool

| | | | | ($\mu$g/1 g of stool) Day 7 after end of |
|---|---|---|---|---|
| | Day 0 | Day 7 | Day 14 | administration |
| Ammonia | 457 | 357 | 346 | 443 |
| Phenol | 18 | 5 | 4 | 17 |
| Cresol | 41 | 24 | 21 | 41 |
| Indole | 38 | 11 | 2 | 36 |
| Skatole | 16 | 4 | 2 | 13 |

Administration of lactulose decreased significantly the concentration of toxic low molecule nitrides such as ammonia. 7 days after the end of the administration, the concentration of those substances, however, returned to the level prior to the administration.

Example 2

A daily dose of 16–24 mg of lactulose was administered orally to 33 renal hemodialysis patients complaining of pruritus cutaneus for 8 weeks continuously and their blood was collected in week 4 and week 8 for the determination of blood uremic toxins. The results are shown in Table 2.

TABLE 2

Effect of lactulose on uremic toxins

| | Week 0 | Week 4 | Week 8 |
|---|---|---|---|
| $\beta_2$ microglobulin (mg/l) | 25.6 ± 1.1 | 25.6 ± 1.3 (ns) | 26.5 ± 2.6 (ns) |
| Indole sulfate ($\mu$g/ml) | 33.1 ± 2.2 | 29.8 ± 2.2 (−10.0% ‡) | 27.6 ± 2.7 (−16.5% ‡‡) |
| p-Cresol ($\mu$g/ml) | 7.66 ± 0.6 | 6.82 ± 0.7 (−10.9% ‡) | 6.35 ± 0.9 (−17.0% ‡) |
| Phenol ($\mu$g/ml) | 1.76 ± 0.3 | 1.73 ± 0.3 (ns) | 1.56 ± 0.3 (ns) |
| Methylguanidine (nMOL/ml) | 4.57 ± 0.3 | 4.03 ± 0.4 (−11.7% ‡‡) | 3.96 ± 0.3 (−13.4% ‡‡) |
| Guanidinosuccinic acid (nMOL/ml) | 21.4 ± 1.8 | 20.9 ± 1.9 (ns) | 18.6 ± 2.2 (−13.1% ‡‡) |
| Methylguadinine/ Creatinine (%) | 37.2 ± 2.1 | 32.5 ± 2.1 (−12.6% ‡‡) | 32.8 ± 1.8 (−11.8% ‡‡) |

Mean ± Standard Error
‡ $p < 0.05$
‡‡ $p < 0.01$

Blood concentration of uremic toxins such as $\beta_2$-microglobulin, indole sulfate, p-cresol, phenol, methylguanidine and guanidinosuccinic acid is extremely higher than that of healthy subjects but administration of lactulose significantly decreased indole sulfate, p-cresol, methylguanidine and guanidinosuccinic acid.

Example 3

Relation between the 4 substances, indole sulfate, p-cresol, methylguadinine and gudininosuccic acid that showed significant decrease by administration of lactulose and effect on alleviation of pruritus cutaneus was examined. Each case showed more than 10% decrease after the administration. Relation between the number of uremic toxins decreased and the rate of efficacy is shown in Table 3.

TABLE 3

Number of substances decreased and rate of efficacy in 25 cases showing alleviation of pruritus cutaneus

| Number of substances decreased | Number of cases | Number of effective cases | Rate of efficacy (%) | Number of ineffective cases | Rate of inefficacy (%) |
|---|---|---|---|---|---|
| 4 | 7 | 7 | 100 | 0 | 0 |
| 3 | 6 | 6 | 100 | 0 | 0 |
| 2 | 8 | 6 | 75 | 2 | 25 |
| 1 | 10 | 6 | 60 | 4 | 40 |
| 0 | 0 | 0 | 0 | 2 | 100 |

Not a single substance but several substances combined together are considered to be responsible for induction of pruritus cutaneus, and the more the number of the substances was decreased by more than 10% by administration of lactulose, the better pruritus cutaneus was alleviated. This proves that decline in the blood concentration of uremic toxins by administration of lactulose is effective on better alleviation of pruritus cutaneus.

Example 4

After breakfast and dinner, a total of 16–24 g of lactulose was administered orally to the 33 renal hemodialysis patients complaining of pruritus cutaneus for 8 weeks.

According to the criteria for the severity of pruritus cutaneus in 5 scores (extremely itchy, very itchy, itchy, slightly itchy, no symptom), the effect of administration of lactulose on pruritus cutaneus was determined and evaluated in 5 grades (remarkably effective, effective, slightly effective, unchanged and aggravated) by comparing the scores at the start of and after the administration. The effect of lactulose on pruritus cutaneus and its change with time are shown in Tables 4 and 5, respectively.

TABLE 4

Effect of lactulose on pruritus cutaneus

|  | Number | (%) |
|---|---|---|
| Remarkably effective (pruritus cutaneus score improved by at least 3 grades) | 1 | 3.0 |
| Effective (pruritus cutaneus score improved by not more than 2 grades) | 12 | 36.4 |
| Slightly effective (pruritus cutaneus score improved by not more than 1 grade) | 12 | 36.4 |
| Unchanged (pruritus cutaneus score unchanged) | 8 | 24.2 |
| Aggravated (pruritus cutaneus score aggravated) | 0 | 0 |

Administration of lactulose alleviated itching in 75.8% of the pruritus cutaneus patients.

TABLE 5

Change with time in effect of lactulose on pruritus cutaneus

|  | Severe pruritus cutaneus patients (extremely itchy + very itchy) | Light pruritus cutaneus patients (itchy + slightly itchy) |
|---|---|---|
| Before administration | 54.6% | 9.0% |
| 2 weeks after administration | 27.3 | 27.3 |
| 4 weeks after administration | 12.0 | 48.6 |
| 8 weeks after administration | 13.6 | 50.0 |

The percentage of the severe pruritus cutaneus patients decreased from 54.6% prior to the administration down to 12% and that of the light pruritus cutaneus patients increased from 9.0% to 50% 4 weeks after the start of administration of lactulose.

INDUSTRIAL APPLICABILITY

Oligosaccharides like, but not limited to, fructo-oligosaccharide, galactooligosaccharide, isomalto-oligosaccharide, malto-oligosaccharide, lacto-sucrose and xylo-oligosaccharide, in particular, disaccharides such as, but not limited to, lactulose, trehalose, rhamnose and lactitol are effective on the treatment of renal failure or its complications associated with renal hemodialysis patients, especially, pruritus cutaneus.

We claim:

1. A method of treating pruritus cutaneus resulting from hemodialysis, comprising administering to a patient in need thereof, a therapeutically effective amount of a pharmaceutical composition in unit dosage form consisting essentially of at least one oligosaccharide as the active ingredient, and a pharmaceutically acceptable excipient.

2. A method of treating pruritus cutaneus resulting from renal failure, comprising administering to a patient in need thereof, a therapeutically effective amount of a pharmaceutical composition in unit dosage form consisting essentially of at least one oligosaccharide as the active ingredient, and a pharmaceutically acceptable excipient.

3. The method as claimed in claim 2 wherein said oligosaccharide is selected from the group consisting of fructo-oligosaccharide, galacto-oligosaccharide, isomalto-oligosaccharide, malto-oligosaccharide, lacto-oligosaccharide, xylo-oligosaccharide and mixtures thereof.

4. The method as claimed in claim 2 wherein said at least one oligosaccharide is a disaccharide.

5. The method as claimed in claim 4 wherein said disaccharide is selected from the group consisting of lactulose, trehalose, rhamnose, lactitol and mixtures thereof.

6. The method as claimed in claim 4 wherein said disaccharide is lactulose.

7. A treatment method for ameliorating pruritus cutaneus resulted from hemodialysis, in a patient in need of said treatment, comprising administering a pharmaceutical composition to said patient in an amount effective to provide said amelioration, said pharmaceutical composition consisting essentially of, as an active ingredient, at least one oligosaccharide, and a pharmaceutical excipient, said pharmaceutical composition being present in a unit dosage form containing an amount of said at least one oligosaccharide sufficient for improving said pruritus cutaneus.

* * * * *